United States Patent
Ifukube et al.

(10) Patent No.: US 6,735,315 B1
(45) Date of Patent: May 11, 2004

(54) ELECTRIC ARTIFICIAL LARYNX

(75) Inventors: Tohru Ifukube, Hokkaido (JP); Akira Koikeda, Hokkaido (JP); Yasunori Sugai, Hokkaido (JP); Shinichi Takabatake, Hokkaido (JP); Yoshinori Yamaguchi, Hokkaido (JP)

(73) Assignee: Densi, Inc., Sapporo (JP)

( * ) Notice: Subject to any disclaimer, the term of this patent is extended or adjusted under 35 U.S.C. 154(b) by 0 days.

(21) Appl. No.: 09/486,782

(22) PCT Filed: Sep. 7, 1998

(86) PCT No.: PCT/JP98/04001
§ 371 (c)(1),
(2), (4) Date: Jun. 16, 2000

(87) PCT Pub. No.: WO99/12501
PCT Pub. Date: Mar. 18, 1999

(30) Foreign Application Priority Data

Sep. 8, 1997 (JP) ............................................. 9-261029

(51) Int. Cl.[7] .................................................. A61F 2/20
(52) U.S. Cl. .............................................. 381/70; 623/9
(58) Field of Search ................................ 381/70; 623/9

(56) References Cited

U.S. PATENT DOCUMENTS

| | | | | |
|---|---|---|---|---|
| 4,028,492 A | * | 6/1977 | Sickel | 381/70 |
| 4,272,647 A | * | 6/1981 | Veit et al. | 381/70 |
| 4,292,472 A | * | 9/1981 | Lennox | 381/70 |
| 5,812,681 A | * | 9/1998 | Griffin | 381/70 |

* cited by examiner

Primary Examiner—Xu Mei
Assistant Examiner—Brian Pendleton
(74) Attorney, Agent, or Firm—Stephen M. Chin, Esq.; Reed Smith LLP

(57) ABSTRACT

This electric artificial larynx 1 comprises a sound source generating unit 3 which is held by interposition means 2 attached directly or indirectly to the human body 10 and can be always placed near the cervical region 10*a* and a portable controller 4 which is separated from the sound source generating unit 3 and operates the sound source generating unit 3. The controller 4 preferably comprises a control signal generating unit which includes a sensor for detecting ID biological information or a switch 12 for supplying a signal and a control unit 16 which drives and controls the sound source generating unit 3 in response to a signal from the control signal generating unit and has a power source unit 15 for supplying power to the sound source generating unit 3. The sound source generating unit 3 may be caused to output a sound using sound source data based on the voice data of an operator before an operation for removing the larynx, or storage means for storing sound source data for singing a song may be provided in the controller 4 detachably.

4 Claims, 9 Drawing Sheets

|  | B00 | B01 | B02 | B03 | B04 | •••• |
|---|---|---|---|---|---|---|
| A00 | D00 | D01 | D02 | D03 | D04 | •••• |
| A01 | D10 | D11 | D12 | D13 | D14 | •••• |

⋮

ELECTRIC ARTIFICIAL LARYNX

BACKGROUND OF THE INVENTION

1. Field of the Invention

The present invention relates to an electric artificial larynx which is an apparatus used by a person who cannot vocalize owing to an operation for removing the larynx for the reason of laryngeal cancer or the like to vocalize again.

2. Description of the Related Art

When the larynx is removed, the vocal cords which are a sound source for vocalizing are lost. Therefore, a person whose vocal cords have been removed cannot vocalize. However, even when the vocal cords are lost, articulating organs such as the tongue and lips still remain. Therefore, if a sound source can be formed in place of the vocal cords by any means, vocalizing which may be incomplete is possible.

Substitute vocalization means based on this principle include gullet vocalization, operational sound language preservation, electric artificial larynx and the like. The gullet vocalization is that a belch-like air stream is burst forth to make sounds which are changed by the tongue, lips and the like for vocalizing. This gull vocalization does not require an extra device and enables a person having no vocal cords to vocalize freely anywhere once he/she masters this technique. However, the gull vocalization involves such defects that it takes time to master this gull vocalization, it is difficult for a sickly person or aged person to master this and it is impossible to vocalize loud.

An example of the operational sound language preservation includes an artificial vocal organ disclosed by Japanese Patent Application Laid-open No. Hei 6-133993. Since this artificial vocal organ is buried in the body, there is no trouble of carrying an extra device and a person having this artificial vocal organ can vocalize freely anywhere like the gull vocalization. However, the artificial vocal organ requires an extra surgical operation on the trachea and must be exchanged and cleaned every about 8 weeks due to the generation of adherents or bacteria.

The electric artificial larynx forms a substitute sound source in place of the vocal cords mechanically or electro-mechanically and this substitute sound source is introduced into the oral cavity to enable a person who had an operation for removing the larynx to vocalize. This electrical artificial larynx is used in such a manner that it is pressed against the cervical region of the human body and a switch is operated with a finger when the person wants to vocalize. Therefore, it has such troubles that this device must always be carried and the work of pressing the switch against the cervical region and operating the switch must be carried out every time the person vocalizes.

However, this electrical artificial larynx does not need long-time training like the gull vocalization and can be used by a sickly person and aged person with ease. Unlike the artificial vocal organ, a special surgical operation or regular exchange and washing are not necessary and the electrical artificial larynx is very easy to handle. Since the electrical artificial larynx has such advantages, it is indispensable as substitute vocalization means.

Conventional electrical artificial larynxes have a switch for turning on and off a substitute sound source. A person who had an operation for removing the larynx only turns on and off the substitute sound source by operating this switch with his/her finger to vocalize. It is a well known fact that when a non-handicapped person vocalizes, he/she changes the basic frequency and sound volume of the vocal cords according to the contents of vocalizing to express accent and intonation or change the tone of voice. In contrast to this, it is impossible to express accent and intonation or change the tone of voice with substitute sound sources formed by the conventional electric artificial larynxes because they are a substitute sound source having a fixed basic frequency and a fixed sound volume. As a result, they have a serious problem that the person who had an operation for removing the larynx can vocalize only in an unnatural voice.

The influence that this problem exerts upon the daily life of the person who had an operation for removing the larynx is extremely large. That is, a lot of mental anguish has been complained that he/she cannot be understood what his he/she says, his/her delicate feeling cannot be expressed, it is hard to vocalize over the phone, or vocalizing with another person makes him/her feel ashamed or irritated, or surprises another person because his/her voice is unnatural.

It is needless to say that the basic frequency and sound volume of the vocal cords must be changed to sing a song. However, since the conventional electric artificial larynxes can form only a sound source having a fixed basic frequency and a fixed sound volume as described above, it is impossible to sing a song with the electric artificial larynxes.

To solve the above problems, the applicants jointly developed electric artificial larynxes as disclosed by Japanese Patent Application Laid-open Nos. Hei 7-433 and Hei 8-265891. The electric artificial larynx disclosed by Japanese Laid-open Patent Application No. 7-433 makes it possible to express accent and intonation or change the tone of voice while vocalizing by controlling the basic frequency and sound volume of a substitute sound source output from an acoustic converter according to information on respiration and the like detected by biological information detecting means. Therefore, it is possible to vocalize in a more natural voice.

Information for controlling the basic frequency and sound volume is recorded in an information recording medium in advance so that the basic frequency and sound volume of the substitute sound source output from the acoustic converter can be controlled according to information read from this information recording medium. Therefore, especially when information for controlling the basic frequency and sound volume is predetermined as in the case that words and sentences which are used frequently are vocalized or a song is sung, a great effect is obtained.

Further, the electric artificial larynx disclosed by Japanese Laid-open Patent Application No. 8-265891 comprises a switch for turning on and off a sound produced from an acoustic converter and a unit for changing the basic frequency and volume of the sound which is integrated with the switch. Therefore, operation efficiency is greatly improved, accent and intonation are easily expressed, a more natural voice can be obtained, and the device can be reduced in size and cost.

Since a piezoelectric sounding body or electronic sounding body is used as the acoustic converter, reductions in size and cost are possible and a more natural voice can be obtained due to quick response and a wide frequency band.

Thus, the electric artificial larynxes developed by the applicant solve the problems of the prior art, greatly improve the quality of sound, produce a sound similar to a human voice and enhance convenience.

However, the electric artificial larynxes disclosed by the above publications still have a problem with operation efficiency which is one of the defects of the prior art. That is, all the electric artificial larynxes of the prior art produce a sound by applying a sound source generating unit to the cervical region of an operator and operating a switch for turning on and off the sound source while holding the body with one hand. The body of each of the devices incorporates a control circuit for controlling the sound source generating unit and a power source unit for supplying power to the sound source generating unit in addition to the sound source generating unit and has a total weight of more than 100 g and a length of more than 10 cm.

The body of this electric artificial larynx must be brought up to the cervical region each time an operator wants to vocalize, which is an operation trouble for the operator (a person whose had an operation for removing the larynx). Since the electric artificial larynx must be operated by holding the body with one hand, only the other hand can be used while vocalizing. Therefore, the operator cannot take a memo while talking on the telephone or cannot vocalize when work requiring both hands is carried out with the result that good communication cannot be made, thereby making it difficult for a person who had an operation for removing the larynx to return to the society, which is a serious problem to be solved.

SUMMARY OF THE INVENTION

It is an object of the present invention which has been made to solve the above problem to provide an electric artificial larynx which improves operation efficiency by eliminating the trouble of bringing a sound source generating unit up to the cervical region each time an operator vocalizes. It is another object of the present invention to provide an electric artificial larynx which enables an operator to use both hands when vocalizing. It is still another object of the present invention to provide an electric artificial larynx which can reduce the size of a sound source generating unit and does not provide an operator with a feeling of physical disorder when only the sound source generating unit is attached near the cervical region.

According to a first aspect of the present invention, there is provided an electric artificial larynx which comprises a sound source generating unit which is held by interposition means attached directly or indirectly to the human body and can be always placed near the cervical region and a portable controller which is separated from the sound source generating unit and can operate the sound source generating unit. Therefore, only the sound source generating unit can be placed near the cervical region and the controller can be stored in clothes or the like. As a result, it is not necessary to bring the sound source generating unit up to the cervical region by hand each time an operator vocalizes, thereby greatly improving operation efficiency. In addition, the controller is devised to enable the operator to use both hands freely when vocalizing. The interposition means is a band wound round the neck, an accessory covering the vocal cords, a member projecting toward the cervical region from a device attached to the arm or shoulder, or the like.

According to a second aspect of the present invention, there is provided an electric artificial larynx wherein the above controller comprises a control signal generating unit which includes a sensor for detecting biological information or a switch for supplying a signal and a control unit which drives and controls the sound source generating unit in response to a signal from the control signal generating unit and has a power source unit for supplying power to the sound source generating unit. Therefore, the sound source generating unit can be easily controlled by the sensor or the like of the controller and supplied with power by the power source unit of the control unit. The sensor for detecting biological information may be an exhalation sensor for detecting the exhalation of an operator, a muscle potential sensor for detecting the potential of muscle near the mouth portion of an operator, a sensor for detecting the movements of ear holes which are considered as the movements of jaws, a brain wave sensor for detecting changes in brain waves which are considered as the movement of the mouth or the will of vocalizing, or the like.

According to a third aspect of the present invention, there is provided an electric artificial larynx wherein the interposition means is a band wound round the neck and the control signal generating unit is an exhalation sensor for detecting biological information attached to the band. When the sound source generating unit is attached to the band, it can be contacted to the cervical region and can be always placed on the cervical region unless the band comes off from the neck. In addition, as the exhalation sensor can be attached to the band, another device for attaching the sensor is not required, thereby making it possible to reduce the size of the apparatus and easy to handle the apparatus. Further, since the exhalation sensor can be attached to the band, both hands are free and can be used to do other work while vocalizing.

According to a fourth aspect of the present invention, there is provided an electric artificial larynx wherein the control signal generating unit comprises a pressure switch fixed to a finger sack and a pressure sensor which is operated by this pressure switch. Since the pressure sensor is operated by the pressure switch fixed to the finger sack, the sound source generating unit can be controlled by slight changes in the pressure of a finger. Therefore, the sound source generating unit can be controlled while other work, for example, carrying a book or reading a book can be continued with a hand having the finger sack.

According to a fifth aspect of the present invention, there is provided an electric artificial larynx which comprises a sound source generating unit for generating a sound source by opposing a vibration sheet to a shaft which operates together with the coil of a voice coil motor and butting this shaft against the vibration sheet intermittently and a controller for controlling this sound source generating unit, wherein the shaft or the coil is supported by an elastic member both ends or peripheral end of which is fixed to the yoke of the voice coil motor, and at least the coil and a coil holder are stored in the yoke. In this invention, the weight of the apparatus can be reduced by using the voice coil motor, rubber supporting the shaft or coil is fixed to the yoke, and at least the coil and the coil holder are stored in the yoke, thereby making it possible to flatten the yoke without increasing the thickness thereof. As a result, even when the sound source generating unit is always placed near the cervical region, it does not give an operator a feeling of physical disorder. As the elastic member is used rubber, sheet spring, resin having elasticity or the like.

According to a sixth aspect of the present invention, there is provided an electric artificial larynx which comprises a sound source generating unit for generating a sound source by opposing a vibration sheet to a shaft which operates together with the coil of a voice coil motor and butting this shaft against the vibration sheet intermittently and a controller for controlling this sound source generating unit, wherein the sound source generating unit is installed such that it can contact the cervical region, and the controller is separated from the sound source generating unit and can be stored in part of clothing covering the human body. Therefore, only the sound source generating unit whose weight has been reduced can be always placed on the cervical region. As a result, the trouble of bringing the sound source generating unit up to the cervical region each time an operator vocalizes is eliminated, thereby improving operation efficiency. Since the heavy controller can be stored in part of clothes, only the small-sized sound source generating unit can be seen, which greatly reduces a third person's feeling of difference. The clothing material may be clothes such as a business suit, trousers, coat, blouse or slacks, pouch to be put on the waist, small bag to be hung from the shoulder, hat to be put on the head, or the like.

According to a seventh aspect of the present invention, there is provided an electric artificial larynx which comprises a sound source generating unit for generating a sound source by opposing a vibration sheet to a shaft which operates together with the coil of a voice coil motor and butting this shaft against the vibration sheet intermittently and a controller for controlling this sound source generating unit, wherein the sound source generating unit is separated from the controller, and the thickness of the sound source generating unit is set to 5 to 15 mm. Therefore, the sound source generating unit can be made light in weight and small in size, thereby making it possible to place it always on the cervical region. As a result, the trouble of bringing the sound source generating unit to the cervical region each time an operator vocalizes is eliminated, thereby improving operation efficiency. Since the thickness of the sound source generating unit is 5 to 15 mm, it does not project too much even when it is placed near the cervical region, which does not give an operator or a third person a feeling of difference.

According to an eighth aspect of the present invention, there is provided an electric artificial larynx wherein the controller has a power source for driving a voice coil motor. Therefore, the power source for control can be shared by the sound source generating unit.

According to a ninth aspect of the present invention, there is provided an electric artificial larynx wherein the sound source generating unit is attached to interposition means fixed to the human body or a clothing material covering the human body and can be moved in a predetermined direction based on the interposition means when or right before a sound is produced from the sound source generating unit. Therefore, while the sound source generating unit is attached to the interposition means, it is not contacted to the cervical region but can be contacted to the cervical region only at the time of vocalizing. As a result, when an operator is silent, he/she does not feel the application of the sound source generating unit on the cervical region and feels free from the application.

According to a tenth aspect of the present invention, there is provided an electric artificial larynx wherein the control of the sound source generating unit by the controller is carried out wireless and the supply of power to the sound source generating unit is carried out by a power source placed in a portion other than the controller. Since the sound source generating unit is controlled wireless, a control lead wire for connecting the sound source generating unit to the controller is not required, thereby making it possible to increase the freedom of installing the controller. For example, the power source of the power source generating unit is stored in a pouch put on the waist and the controller is shaped like a wristwatch or mechanical pen so that it can be placed around an exhalation sensor.

According to an eleventh aspect of the present invention, there is provided an electric artificial larynx which has a controller for causing the sound source generating unit to output a sound using sound source data based on the voice data of an operator before an operation for removing the larynx. Since the output sound is based on the voice data of the operator before the operation, he/she can vocalize infinitely in a voice similar to his/her own voice before the operation.

According to a twelfth aspect of the present invention, there is provided an electric artificial larynx which comprises a controller having sound source data based on the voice data of an operator before an operation for removing the larynx and a sound source generating unit for outputting a sound using the sound source data. The voice data of the operator before the operation is stored in the control unit, thereby making it possible for the operator to vocalize in a voice similar to his/her own voice before the operation.

According to a thirteenth aspect of the present invention, there is provided an electric artificial larynx which comprises a sound source generating unit in place of the vocal cords and a controller for operating the sound source generating unit, wherein memory means for storing sound source data for singing a song is provided in the controller detachably. Therefore, an unlimited number of songs can be sung theoretically by storing many songs in many storage means.

BRIEF DESCRIPTION OF THE DRAWINGS

These and other objects and advantages of the present invention will become clear by the following description of preferred embodiments of the present invention with reference to the accompanying drawings, wherein.

DETAILED DESCRIPTION OF THE PREFERRED EMBODIMENTS

The present invention will be described in detail with reference to the accompanying drawings. A first preferred embodiment of the present invention and modifications thereof will be first described with reference to FIGS. 1 to 11.

Figure 1:
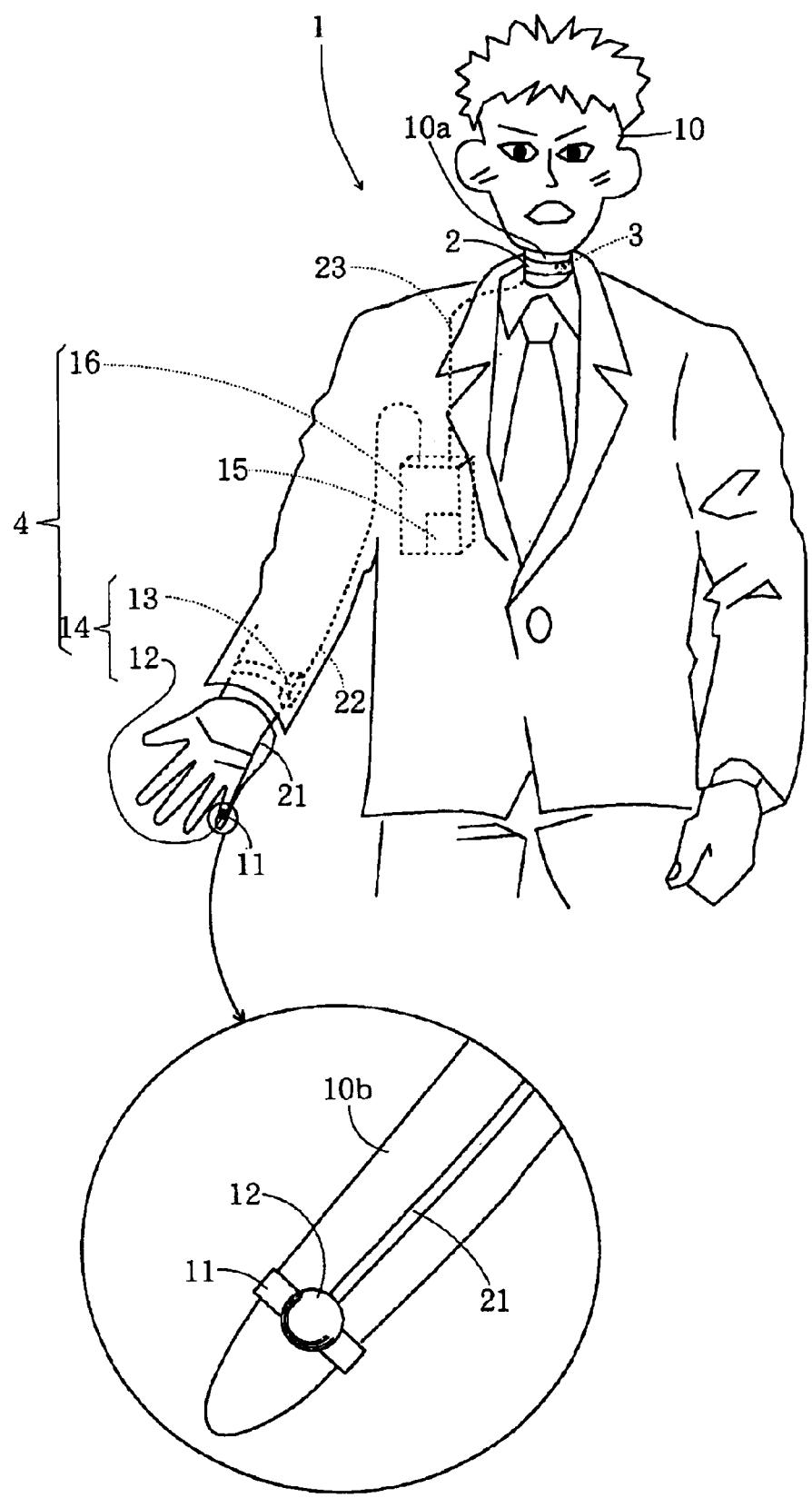
FIG. 1 is a diagram showing the whole constitution of an electric artificial larynx according to a first preferred embodiment of the present invention and an enlarged view of a fingertip portion.

FIG. 1 shows the whole constitution of a preferred electric artificial larynx 1. This electric artificial larynx 1 comprises a sound source generating unit 3 which is a substitute sound source held by a band 2 which is an interposition means attached to the cervical region of the human body 10 and able to be always placed near the cervical region 10a of the human body 10 and a portable controller 4 which is separated from the sound source generating unit 3 and operates the sound source generating unit 3.

The controller 4 comprises a control signal generating unit 14 which includes a pressure switch 12 fixed to a finger sack 11 placed on a little finger 10b and a pressure sensor 13 operated by the pressure switch 12, and a control unit 16 which drives and controls the sound source generating unit 3 in response to a signal from this control signal generating unit 14 and has a power source unit 15 for supplying power to the sound source generating unit 3.

The pressure switch 12 contains air therein which operates the pressure sensor 13 through a transmission tube 21 when the volume of the inside air becomes small. A connection cable 22 for transmitting a signal from the pressure sensor 13 to the control unit 16 and for supplying the power of the power source unit 15 to the pressure sensor 13 is provided between the control unit 16 and the pressure sensor 13. Further, a power supply cable 23 for supplying power controlled by the control unit 16 to the sound source generating unit 3 and supplying power for operating a pressing unit which will be described hereinafter is provided between the control unit 16 and the sound source generating unit 3.

Figure 2:
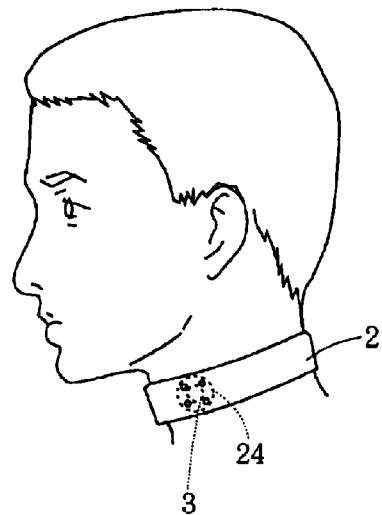
FIG. 2 is a diagram showing that the sound source generating unit of the electric artificial larynx of FIG. 1 is attached.
Figure 3:
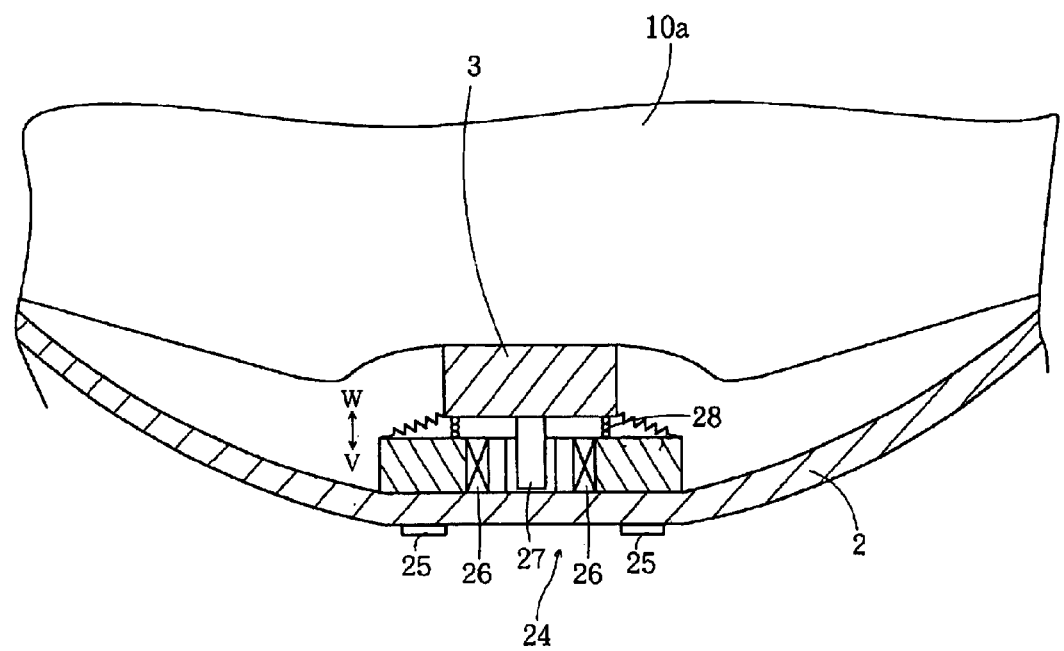
FIG. 3 is a partial sectional view showing the relationship between the sound source generating unit and a solenoid unit when seen from the top of FIG. 2.

As shown in FIG. 2 and FIG. 3, the band 2 can extend or contract freely, has predetermined elongation strength and is wound round the entire neck including the cervical region 10a. The sound source generating unit 3 is strongly pressed against the cervical region 10a by a solenoid unit 24 which is a pressing unit at the time of vocalizing.

As shown in FIG. 3, the sound source generating unit 3 and the solenoid unit 24 are covered with the band 2 and attachment portions 25 for attaching the solenoid unit 24 are exposed to the outside. The solenoid unit 24 is turned on when an electric current runs through coils 26. Therefore, when an operator is silent, an iron movable piece 27 fixed to the sound source generating unit 3 is pulled in a direction V shown by an arrow shown in FIG. 3 in defiance of the extension force of springs 28, and the sound source generating unit 3 retreats in the direction V shown by the arrow in FIG. 3. When the solenoid unit 24 is turned off by a signal from the pressure sensor 13 when or right before the operator vocalizes, the springs 28 extend in a direction W shown by an arrow and the sound source generating unit 3 is strongly pressed against the cervical region 10a.

When the solenoid unit 24 is turned off, the sound source generating unit 3 moves in the direction of the cervical region 10a. However, when the solenoid unit 24 is turned on, the sound source generating unit 3 may move in the direction of the cervical region 10a. When pressing force is fully generated by the band 2 without strongly pressing the sound source generating unit 3 against the cervical region 10a by the solenoid unit 24, the solenoid unit 24 may be omitted.

Figure 4:
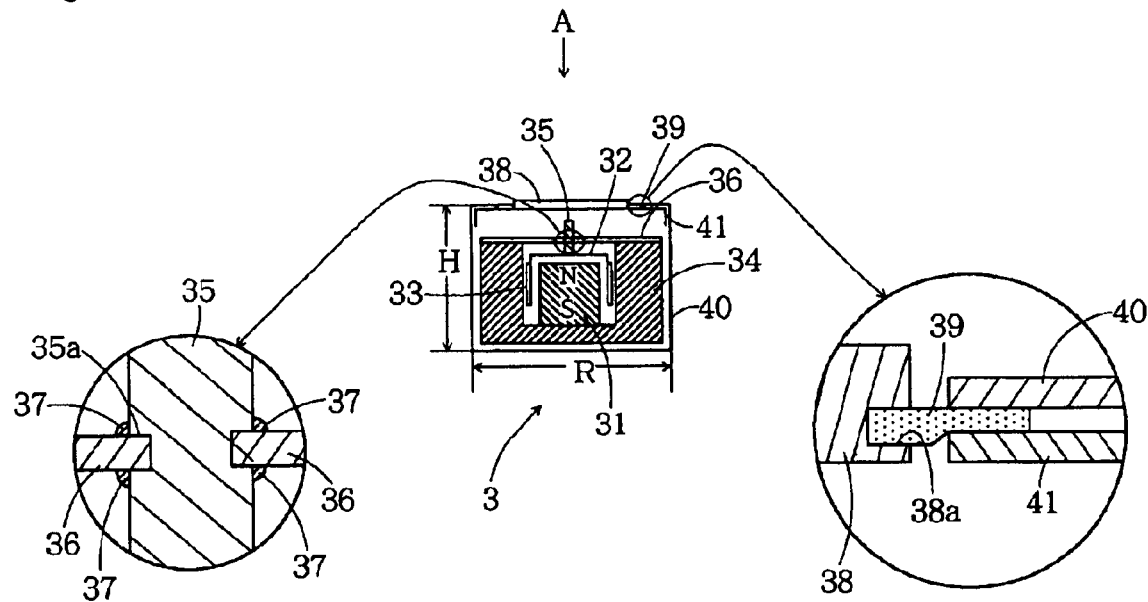
FIG. 4 is a sectional view and a partially enlarged view of the sound source generating unit used in the electric artificial larynx of FIG. 1.
Figure 5:
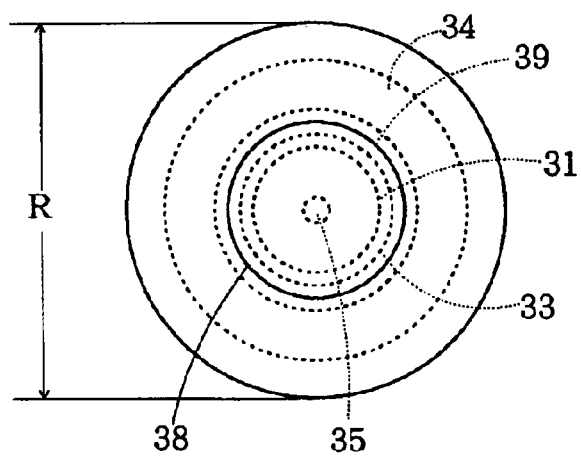
FIG. 5 is a plan view of FIG. 4 when seen from a direction shown by an arrow A.

The sound source generating unit 3 is a voice coil motor theoretically whose structure is such as shown in FIG. 4 and FIG. 5. That is, the motor comprises a cylindrical magnet 31 whose both ends are magnetized N and S, a cylindrical coil holder 32 surrounding the magnet 31, a coil 33 wound round the coil holder 32 and a yoke 34 surrounding the coil 33.

The coil holder 32 and the coil 33 are completely stored in the yoke 34. A shaft 35 is provided at the center of the coil holder 32 and fixed to circular rubber 36 bonded and fixed to the side end portion of the opening of the yoke 34. To fix the shaft 35, as shown in an enlarged portion of FIG. 4, a cut-out 35a is formed in the outer surface of the shaft 35, rubber 36 is inserted into this cut-out 35a, and an adhesive 37 is applied to portions around the cut-out 35a. This adhesive 37 may not be used.

A vibration sheet 38 made from an urethane resin is opposed to the shaft 35. A doughnut-shaped foamed rubber material 39 is provided at the periphery of the vibration sheet 38 and fixed to an outer frame 40. The rubber material 39 is mated with a circular stepped portion 38a formed in the vibration sheet 38 and its peripheral portion is sandwiched between the outer frame 40 and a sandwiching member 41 to be fixed. A male screw (not shown) is formed at the peripheral portion of the sandwiching member 41 and a portion corresponding to the male screw of the outer frame 40 is threaded (not shown) so that the rubber material 39 is sandwiched by turning the sandwiching member 41 to proceed.

The material of the vibration sheet 38 may be other resin material such as polycarbonate or metal material. To soften the quality of sound produced from the vibration sheet 38, a silicone rubber film having a thickness of 0.2 to 0.4 mm (not shown) may be formed on the entire surface of the vibration sheet 38 against which the shaft 35 is butted. The thickness of this thin silicon rubber film is the most preferably 0.3 mm.

The operation principle of the sound source generating unit 3 is that the shaft 35 goes up in FIG. 4 according to the Fleming's rule when electricity is applied to the coil 33 because a field is formed (gap) between the magnet 31 and the yoke 34. Therefore, the shaft 35 strikes the vibration sheet 38 to produce a sound. When electricity is not applied, the shaft 24 is lowered in FIG. 4 by the rubber 36. In the case of this constitution, the rubber 36 is directly fixed to the yoke 34 and the coil holder 32 and the coil 33 are completely stored in the yoke 34, thereby making it possible to flatten the yoke 34.

This sound source generating unit 3 has a thickness H of 10 mm and a diameter R of 20 mm. When an operator's feeling of physical disorder and appearance seen from a third person are taken into consideration, the thickness H is preferably 5 to 15 mm. The diameter R is preferably 10 to 25 mm when the above points of view are taken, and the size of a place corresponding to the cervical region 10a and the operation force of the voice coil motor are taken into consideration.

Figure 6:
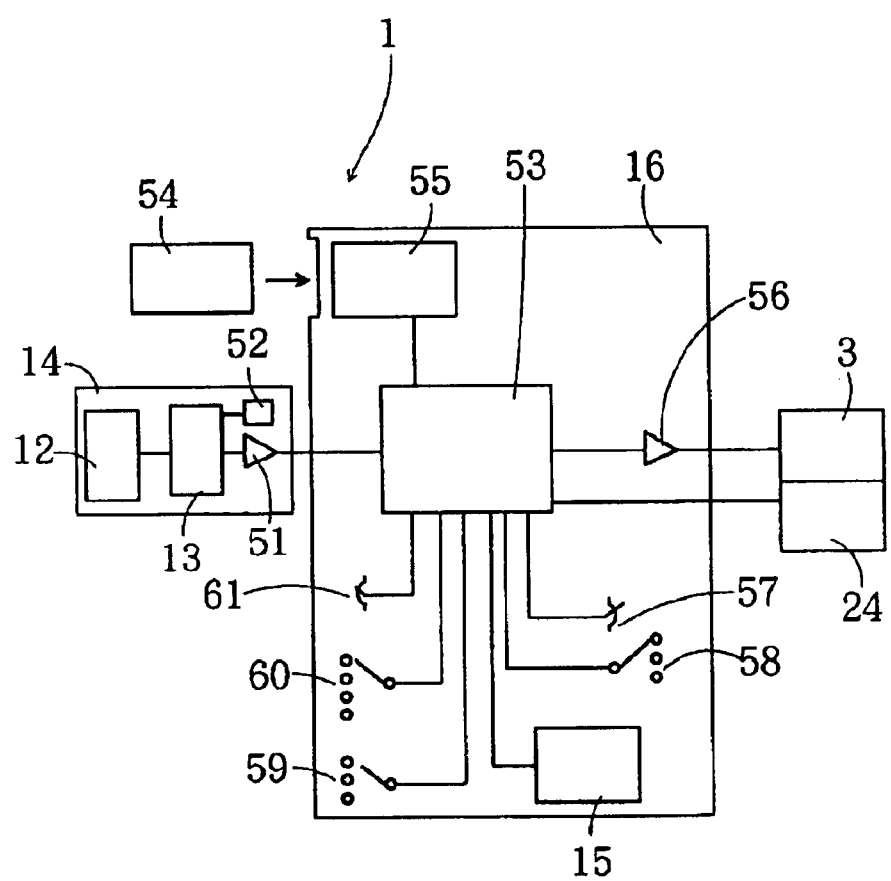
FIG. 6 is a block diagram showing the circuit configuration of the electric artificial larynx of FIG. 1.

The circuit configuration of this electric artificial larynx is shown in FIG. 6. The control signal generating unit 14 comprises a signal amplifying unit 51 and a threshold value control unit 52 for determining a point where the pressure sensor 13 is turned on in addition to the pressure switch 12 and the pressure sensor 13. The control unit 16 comprises a CPU (Central Processing Unit) 53, a memory drive unit 55 for accepting a memory card 54 which is a memory means and transmitting information stored in the memory card 54 to the CPU 53, and a power amplifying unit 56 for amplifying power supply to the power source generating unit 3 in addition to the power source unit 15. The control unit 16 further comprises a sound volume control unit 57 for switching the volume of sound analogically, a basic operation switching unit 58 for switching when the control unit 16 is turned on or off and when an exhalation sensor which will be described hereinafter is used, a mode switching operation unit 59 for switching among a fixed sound (predetermined frequency sound) operation, variable frequency sound operation and a singing function, a song selection operation unit 60 for selecting one from songs stored in the memory card 54, and a tone control unit 61 for changing the tone of a song as the operator desires.

Figures 7, 8:
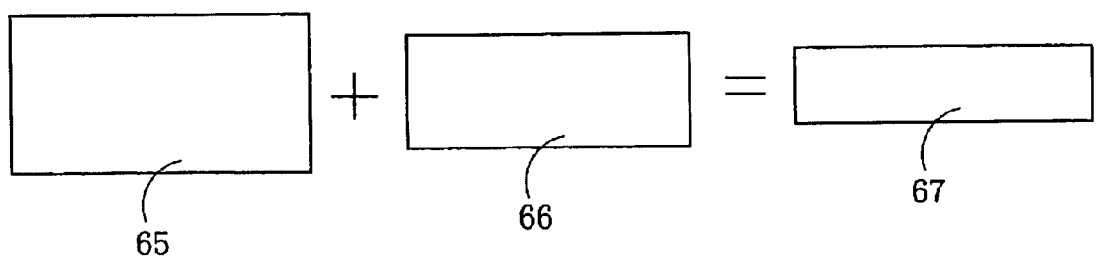
FIG. 7 is a diagram for explaining the internal addresses of a memory card (storage means) used for a singing function added to the electric artificial larynx of FIG. 1.
FIG. 8 is a diagram for explaining a treatment method when a tone control function is added to the singing function of the electric artificial larynx of FIG. 1.

The internal memory addresses of the memory card 54 are shown in FIG. 7. A plurality of songs are recorded in the memory card 54. A first song is recorded at a row address A00 and frequency data D00, D01, D02, . . . on respective sounds from the start of the song are stored at column addresses B00, B01, B02, . . . Similarly, a second song is stored at a row address A01 and frequency data D10, D11, D12, D13, D14, . . . on respective sounds from the start of the song are stored. Further, data on third, fourth and fifth songs are stored similarly. In this embodiment, five songs are stored. The other number of songs may be stored by increasing or decreasing the capacity of the memory. Stated more specifically, the memory address is updated each time the pressure switch 12 is operated. For example, the sound at the address D00 is first output and then changed to the sound at the address D01. To carry out this operation, a simple switch may be used in place of the pressure switch 12.

To execute a singing function, the memory card 54 which records the melodies of songs is inserted into the control unit 16, the mode switching operation unit 59 is switched to a singing function, and a song that an operator wants to sing is selected by the song selection operation unit 60. Thereafter, by operating the pressure switch 12 attached to the finger, the frequency of each sound in accordance with the melody of the song is transmitted to the sound source generating unit 3 to produce a sound. For example, to sing a song starting with "saita, saita, tulip no hana ga", by pressing the pressure switch 12 attached to the finger at "sa", the control unit 16 transmits the sound of the frequency data D00 for the tone of "sa" to the sound source generating unit 3. Thereafter, by pressing the pressure switch 12 again, the tone is switched to the tone of "i" which is the next frequency data D01. Thus, tones for the song are output sequentially. If the shape of the mouth is changed according to the sound of each output tone, a song is sung. One memory card 54 stores tones for a plurality of songs and enables other songs to be stored. Therefore, it is possible to sing various types of music.

It is possible to store sound source data based on the voice data of a person before an operation for removing the larynx and not songs. When the memory card 54 (to be referred to as "memory card 54 for an operator's exclusive use" hereinafter) which stores sound source data based on the voice data of an operator is used, the constitution of the control unit 16 must be slightly changed. Various structures for the control unit 16 are conceivable in this case. At least the following three changes are possible. The first change is that two memory drive units 55 are provided: one is for the memory card 54 for storing songs and the other is for the memory card 54 for an operator's exclusive use. The second change is that the number of the memory drive units 55 is one as it is and a storage portion for storing the data of the memory card 54 for an operator's exclusive use is formed in the control unit 16. When the memory card 54 for an operator's exclusive use is inserted into the memory drive unit 55, the sound source data of the operator is installed in the storage portion of the control unit 16 automatically or by a predetermined switching portion. The third change is that the current singing function is eliminated and a memory drive unit 55 for the memory card 54 for an operator's exclusive is provided instead.

In either case, to produce a sound by the pressure switch 12, the operation switch, etc., the sound source data of the operator stored in the memory card 54 for an operator's exclusive use or installed in the storage portion of the control unit 16 is read. Since the read sound is based on the voice data of the operator before an operation, it is possible to vocalize in a voice similar to that of the operator before an operation.

Sound source data based on the voice data of the operator may be stored in the hard disk of a computer or the like and not the memory card 54 and installed in the storage portion of the control unit 16 by communication means. Further, sound source data based on the voice data of the operator may be stored in an EEPROM chip and incorporated in the control unit 16. Thus, sound source data can be stored in various means and used.

The invention which makes it possible to provide sound source data based on the voice data of the operator and the invention which makes it possible to connect or disconnect storage means (memory card 54) to or from the controller 4 can be applied to a conventional structure comprising a sound source generating unit and a controller which are integrated with each other.

A tone control function provided to the control unit 16 is carried out by operating a tone control portion 61. As shown in FIG. 8, tone control data 66 is added to original tone data 65 read from the memory card 54 to prepare desired frequency data as output data 67. This makes it possible to sharp or flat the original tone, which is very preferred for the operator who cannot control the tone with only his/her vocalization.

The memory card 54 is preferably a flush memory but may be an ordinary EPROM or other card type memory means. A set of the memory means and the memory drive unit may be a set of other storage means and memory drive unit such as a set of an optical magnetic disk and an optical magnetic recording unit or a set of an optical disk and an optical recording unit in addition to a set of the memory card 54 and the memory drive unit 55.

Fixed sound operation switched by the mode switching operation unit 59 is carried out by applying pressure to the pressure switch 12 attached to the finger 10b and transmitting a fixed frequency signal from the control unit 16 to the sound source generating unit 3 when the pressure becomes higher than a certain level to produce a fixed sound. In this case, the same operation is made possible with a simple switch and not the pressure switch 12.

Variable frequency sound operation switched by the mode switching operation unit 59 is carried out by applying pressure to the pressure switch 12 attached to the finger 10b and transmitting a signal having a frequency corresponding to the applied pressure from the control unit 16 to the sound source generating unit 3 when the pressure becomes higher than a certain level to produce a sound. When pressure is further applied, the frequency is changed according to the pressure and a signal having the changed frequency is transmitted to the sound source generating unit 3. That is, when the pressure is small, a low frequency signal is transmitted to the sound source generating unit 3 and when the pressure is high, a high frequency signal is transmitted to the sound source generating unit 3. Thus, the control unit 16 converts the applied pressure into a frequency to change the frequency of a sound produced by the sound source generating unit 3.

The operation of this electric artificial larynx 1 is outlined below.

First, the operator turns on the control unit 16 with the basic operation switching unit 58. The control unit 16 is turned off when this apparatus is removed or when it is certain that the operator will not vocalize for a long time. The volume of sound is set by the sound volume control unit 57 of the control unit 16. Further, fixed sound (fixed frequency sound) operation, variable frequency sound operation or singing function is set by the mode switching operation unit 59.

After the above settings are made, the operator presses the pressure switch 12 when he/she wants to vocalize. When the pressure exceeds a predetermined threshold value, the pressure sensor 13 is activated to transmit a signal informing this to the control unit 16. When the CPU 53 of the control unit 16 receives the signal, it turns off the solenoid unit 24 at first. As a result, the solenoid unit 24 presses the sound source generating unit 3 against the cervical region 10a. Further, the CPU 53 supplies amplified power to the sound source generating unit 3. With the amplified power, the sound source generating unit 3 which has already been pressed against the cervical region 10a transmits a sound to the cervical region 10a and the operator moves his/her mouth in time to the sound so that he/she can vocalize.

Figure 9:
FIG. 9 is a diagram showing the whole constitution of an electric artificial larynx according to a modification of the first preferred embodiment of the present invention.

With reference to FIG. 9, a modification of the first embodiment will be described. The electric artificial larynx 70 of this modification employs a wireless system and not a wire system. The same reference symbols in FIG. 9 denote the same members as those in FIG. 1 and their descriptions are omitted.

The controller 71 of this modification comprises the pressure switch 12, a wristwatch type control unit 72 having a wireless function, the sound source generating unit 3 and a power source unit 73 for the solenoid unit 24. The control unit 72 has its own power source (not shown). The control of power supplied from the power source unit 73 to the sound source generating unit 3 is carried out by the control unit 72 which controls the output portion of the power source unit 73. The control unit 72 may control the input portion of the sound source generating unit 3.

In FIG. 9, the pressure switch 12 and the control unit 72 are connected to each other by a wire. Their interval may be connected wireless. The power source unit 73 is placed in a pouch 74 put on the waist and connected to the sound source generating unit 3 by a wire. If the sound source generating unit 3 and the solenoid unit 24 have their own small-sized power sources, the power source unit 73 is not necessary.

Figure 10:
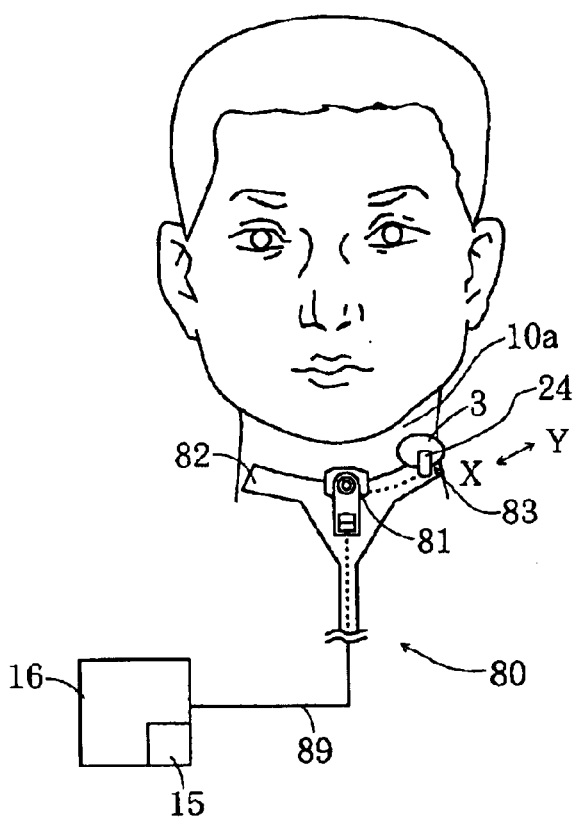
FIG. 10 is a diagram showing another modification of the first embodiment.
Figure 11:
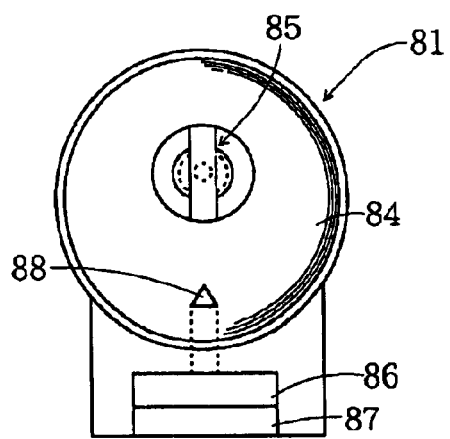
FIG. 11 is a diagram showing an exhalation sensor used in the electric artificial larynx of FIG. 10.

With reference to FIG. 10 and FIG. 11, an electric artificial larynx 80 according to a further modification of the first embodiment will be described. In this modification, an exhalation sensor 81 for detecting biological information and an interposition means 82 for covering only part of the neck, and a moving unit 83 for moving the sound source generating unit 3 are employed.

The exhalation sensor 81 detects the strength of exhalation from the hole of the trachea. The frequency of the sound source generating unit 3 can be changed according to the strength of exhalation. Only the existence of exhalation may be detected, or the sound volume of the sound source generating unit 3 may be controlled according to the strength of exhalation.

The exhalation sensor 81 is mainly composed of a sensor pad 84 formed of a semi-circular soft resin, air valve 85, sensor box 86 storing a sensor and circuit portion 87 having a circuit etc. for controlling the detection threshold of the exhalation sensor 81. The sensor pad 84 has a guide hole 88 for guiding exhalation to the sensor box 86 side.

The interposition means 82 is formed of a T-shaped plastic and supports the exhalation sensor 81 and the sound source generating unit 3. A power and signal transmission cable 89 for connecting the control unit 16 is embedded in the interposition means 82. This interposition means 82 is integrated with a support means attached to the breast or shoulder or fixed to the support means. When the operator puts on clothes over these interposition means, a top portion of the interposition means 82, that is, only the exhalation sensor 81 and a portion therearound can be seen from the outside.

The moving unit 83 absorbs differences among operators who operate this electric artificial larynx 80. That is, in the electric artificial larynxes 1, 70 and 80, the sound source generating unit 3 is pressed against the cervical region 10a, and a sound therefrom is transmitted to the throat through the skin to produce a sound. The position against which the sound source generating unit 3 is pressed differs by each person, and the sound source generating unit 3 cannot be pressed against the same position. Then, the electric artificial larynx 80 has such a structure that the positional relationship between the interposition means 82 fixed to the cervical region 10a and the sound source generating unit 3 is not fixed but can be shifted to any position.

Stated more specifically, the solenoid unit 24 for supporting the sound source generating unit 3 can slide in a direction X and direction Y shown by arrows in FIG. 10 with respect to the interposition means 82. The sound source generating unit 3 can be located at the optimum position for the operator by sliding. The power and signal transmission cable 89 is penetrated through the interposition means 82 and the contact positions of the sound source generating unit 3 and the solenoid unit 24 with the cable 89 are changed by this sliding but both the sound source generating unit 3 and the solenoid unit 24 always receive power supply.

The solenoid unit 24 which is the pressing unit of the electric artificial larynx 80 presses the sound source generating unit 3 against the cervical region 10a when or right before the operator vocalizes and keeps the sound source generating unit 3 away from the cervical region 10a when the operator is silent. The concrete structure of this solenoid unit 24 is the same as shown in FIG. 3 and separates the sound source generating unit 3 from the cervical region 10a in defiance of the spring 28 when the operator is silent. According to this structure, when there is no power for operating the solenoid 24, the solenoid unit 24 is turned off so that the power of the power source unit 15 can be supplied only to the main constituent elements such as the sound source generating unit 3. Even when the solenoid unit 24 does not operate for some reason or other, the sound source generating unit 3 can be pressed against the cervical region 10a by the spring 28 without fail. A sliding type pressing unit may be used in place of the push type solenoid unit 24. When the operator does not feel physical disorder if the sound source generating unit 3 is always pressed against the cervical region 10a, the solenoid unit is always turned off or the other solenoid unit 24 excluding the spring 28 may be removed.

In the electric artificial larynxes 1, 70 and 80, an external switch such as the pressure switch 13 and an exhalation sensor such as the exhalation sensor 81 can be used. A DIP switch (not shown) is provided in the control unit 16 to switch among 60, 80, 100, 120, 140 and 160 Hz for fixed frequency sound operation and among 60 to 220 Hz, 60 to 180 Hz, 60 to 260 Hz, 60 to 300 Hz, 80 to 320 Hz and 80 to 340 Hz for variable frequency operation by means of the external switch and the exhalation sensor. These values are used in the electric artificial larynxes 1, 70 and 80 and merely show one example. Other values may be used. For example, the fixed frequency may be set at intervals of 10 Hz and the number of frequencies may be changed to 7 or more or 5 or less, either one or both of the lower limit and upper limit of the variable frequency may be changed. The switching means may be a rotary switch or select switch besides the DIP switch.

When each of the electric artificial larynxes 1, 70 and 80 is left while the basic operation switching unit 58 which is the main switch is not off, the power of the power source unit 15 runs out. Therefore, when the apparatus in left while it is off and there is no input for a predetermined time, for example, 20 minutes, the sound source generating unit 3 is activated. Further, when this state is continued for a predetermined time, for example, 10 minutes, the sound source generating unit 3 is activated. Thus, the operator's forgetting to turn off the sound source generating unit 3 or the like is prevented. The operation of each time is carried out by driving the sound source generating unit 3 several times in several seconds. To prevent the operator's forgetting to turn off the sound source generating unit 3, the sound source generating unit 3 is activated three times for an interval of 10 minutes, or the interval of activating the sound source generating unit 3 is gradually extended or shortened.

The voice coil motor and the vibration sheet are used to constitute the sound source generating unit 3. A piezoelectric sounding body, an electronic sounding body using an IC and speaker or a vibration sheet system using other motor such as an ultrasonic motor as a drive unit may be used as the sound source generating unit 3.

In the electric artificial larynxes 1, 70 and 80, it is not necessary to hold the body. When the switches of the electric artificial larynxes 1, 70 and 80 attached to a hand are attached to a little finger 10*b*, for example, some works which require both hands, for example, taking a memo while vocalizing over the telephone can be done because the little finger 10*b* does not play an important role in the daily life.

Since a frequency change can be added to a produced sound by the operation of the pressure sensor 13, a voice can be intonated. The sound source generating unit 3 may be fixed to a portion near the cervical region 10*a*, and the control unit 16 may be inserted into a pocket, fixed to a belt or placed in a pouch or pochette. Therefore, even when the electric artificial larynx 1, 70 or 80 is used, it does not stand out much.

Further, these electric artificial larynxes 1, 70 and 80 have a singing function which enables the operator to sing with ease an unlimited number of songs theoretically by exchanging the memory card 54 which is the storage means. The sound source generating unit 3 can be moved by turning the band 2 fixed to the cervical region 10*a*, or the sound source generating unit 3 can be shifted to any position within the range of the interposition means 82, thereby making it possible to make up for differences in the position of the cervical region 10*a* by each person.

Figure 12:
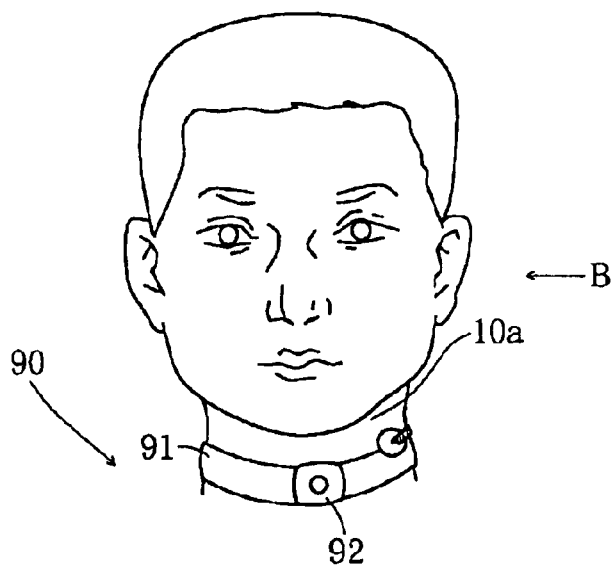
FIG. 12 is a diagram showing the constitution of key parts of an electric artificial larynx according to a second preferred embodiment of the present invention.
Figure 13:
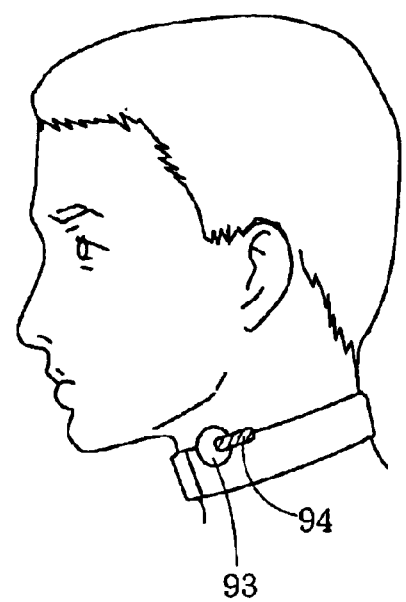
FIG. 13 is a side view when seen from a direction shown by an arrow B of FIG. 12.
Figure 14:
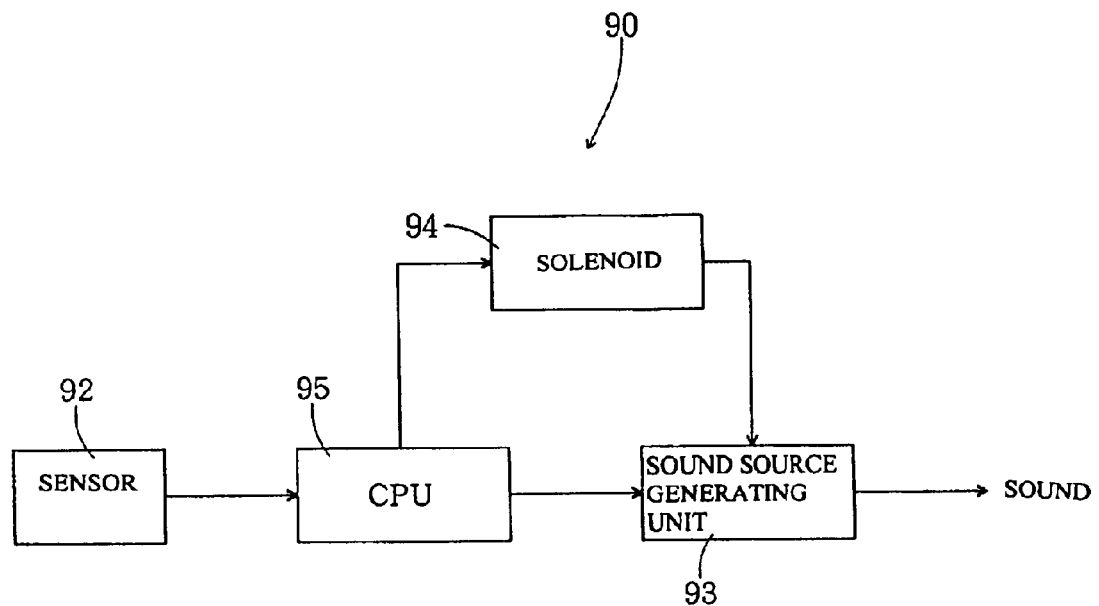
FIG. 14 is a block diagram showing the circuit configuration of the electric artificial larynx of FIG. 12.

A description is subsequently given of an electric artificial larynx 90 according to a second preferred embodiment of the present invention with reference to FIGS. 12 to 14. FIG. 12 and FIG. 13 are a front view and a side view of the electric artificial larynx 90 attached to the cervical region 10*a*, respectively. A band 91 to be attached to the cervical region 10*a* is provided with a sensor 92 for detecting exhalation which is one piece of biological information and a sound source generating unit 93. A solenoid 94 is used to press the sound source generating unit 93 against the cervical region 10*a*.

In FIG. 13, the sensor 92 for detecting exhalation which is one piece of biological information detects exhalation to detect the vocalizing will of the user which is also the operator. The detected signal is transmitted to a CPU 95 which first provides a signal to the solenoid 94 when the signal exceeds a certain threshold value. The solenoid 94 which receives the signal presses the sound source generating unit 93 against the cervical region 10*a* and the CPU 95 provides a signal to the sound source generating unit 93 pressed against the cervical region 10*a* to produce a sound. The sound source generating unit 93 which has already been pressed against the cervical region 10*a* transmits a sound to the cervical region 10*a* and the user moves his/her mouth in time with the sound to vocalize. The sound source generating unit 93 is pressed against the cervical region 10*a* by the solenoid 94 only at the time of vocalizing in such a manner that a sense of oppression more than required should not be given to the cervical region 10*a*. If a sense of oppression does not annoy the user, the sound source generating unit 93 may be always pressed against the cervical region 10*a*. Exhalation is used as means for detecting biological information. The same effect is obtained when other biological information is used and when other external signal is used in place of biological information.

Since this electric artificial larynx 90 is constituted as described above, the following effects are obtained.

1) Both hands can be used freely at the time of vocalizing.
2) Since both hands can be used freely, movement or work which requires both hands becomes easy, thereby making it possible to promote the return of a person who had an operation for removing the larynx to the society.
3) Since the electric artificial larynx 90 is always attached to the cervical region 10*a*, an operator can vocalize right away without pressing the electric artificial larynx 90 against the cervical region 10*a* when he/she intends to vocalize.
4) An operator can vocalize naturally when he/she is looked at.

Preferred embodiments of the present invention have been described above. The present invention is not limited to these embodiments and many changes may be made in design without departing from the spirit and scope of the invention.

As described above, the electric artificial larynx of the present invention is used as a sound source in place of the vocal cords of a person who had an operation for removing the larynx. Particularly, it is very useful for a sickly person, aged person and other person who has the difficulty of mastering gull vocalization. Also, it is very preferred for a person who feels the trouble of operating an electric artificial larynx and a person who wants to use both hands when using the apparatus.

What is claimed is:

1. An electric artificial larynx having a sound source generating unit for generating a sound and a controller which is separated from the sound source generating unit and coupled thereto to operate the sound source generating unit, comprising:

an operating device coupled to the sound source generating unit and responsive to a control signal from the controller to move said sound source generating unit into and out of pressure against the cervical region of a user, and interposition means adapted to support said operating means and said sound source generating unit on a user, said operating device being attached to the interposition means, whereby the sound source generating unit is under pressure against the cervical region when the user is speaking and is out of pressure when the user is not speaking and wherein said sound source comprises a first plunger to actuate said sound source generating unit in generating a sound and wherein said operating device comprises a second plunger to move said sound source generating unit into and out of pressure against the cervical region.

2. The electric larynx of claim 1 wherein said operating means moves said sound source generating unit when, or right before, a sound is produced from the sound source generating unit.

3. An electric artificial larynx having a sound source generating unit for generating a sound and a controller which is separated from the sound source generating unit and coupled thereto to operate the sound source generating unit, comprising:

an operating device coupled to the sound source generating unit and responsive to a control signal from the controller to move said sound source generating unit into and out of contact with the cervical region of a user, interposition means adapted to support said operating means and said sound source generating unit on a user, said operating device being attached to the interposition means; and said sound source comprises a first plunger to actuate said sound unit to generate a sound and wherein said operating device comprises a second plunger to move said sound source generating unit into and out of contact with the cervical region.

4. The electric layrnx of claim 3 wherein said operating means moves said sound source generating unit when, or right before, a sound is produced from the sound source generating unit.

* * * * *